(12) United States Patent
Van Den Heuvel et al.

(10) Patent No.: US 10,485,973 B2
(45) Date of Patent: Nov. 26, 2019

(54) IMPLANTABLE HEARING PROSTHESIS

(71) Applicant: Cochlear Limited, Macquarie University, NSW (AU)

(72) Inventors: Koen Van Den Heuvel, Hove (BE); Jan Janssen, St. Ives (AU)

(73) Assignee: Cochlear Limited, Macquarie University (AU)

( * ) Notice: Subject to any disclaimer, the term of this patent is extended or adjusted under 35 U.S.C. 154(b) by 259 days.

(21) Appl. No.: 13/864,700

(22) Filed: Apr. 17, 2013

(65) Prior Publication Data

US 2013/0296970 A1 Nov. 7, 2013

Related U.S. Application Data

(63) Continuation of application No. 13/124,047, filed as application No. PCT/US2009/060676 on Oct. 14, 2009, now abandoned.

(60) Provisional application No. 61/105,406, filed on Oct. 14, 2008.

(51) Int. Cl.
*A61N 1/08* (2006.01)
*A61N 1/36* (2006.01)

(52) U.S. Cl.
CPC ................................ *A61N 1/36036* (2017.08)

(58) Field of Classification Search
CPC .............. A61N 1/0541; A61N 1/36036; A61N 1/36032
USPC ....................................................... 607/3, 57
See application file for complete search history.

(56) References Cited

U.S. PATENT DOCUMENTS

| | | | | |
|---|---|---|---|---|
| 4,532,930 A | * | 8/1985 | Crosby et al. | 607/57 |
| 6,342,035 B1 | * | 1/2002 | Kroll | H04R 25/606 |
| | | | | 600/25 |
| 6,480,820 B1 | * | 11/2002 | Clopton et al. | 704/203 |
| 6,807,445 B2 | * | 10/2004 | Baumann et al. | 607/57 |
| 7,054,691 B1 | * | 5/2006 | Kuzma et al. | 607/57 |
| 2005/0237549 A1 | | 12/2005 | Santina et al. | |

(Continued)

FOREIGN PATENT DOCUMENTS

| | | |
|---|---|---|
| WO | 94/07342 A | 3/1994 |
| WO | 2006089047 A2 | 8/2006 |
| WO | 2007147418 A1 | 12/2007 |

OTHER PUBLICATIONS

Office Action in Chinese Application No. 200980141013.8, dated Feb. 8, 2013, 8 pages.

(Continued)

*Primary Examiner* — Michael J D'Abreu
(74) *Attorney, Agent, or Firm* — Edell, Shapiro & Finnan, LLC

(57) ABSTRACT

An implantable hearing prosthesis comprising an implantable upgrade module including a pre-processing unit configured to generate audio signals based on microphone information; and a implantable main module, physically separate from and electrically connected to the upgrade module. The implantable main module comprises a sound processing unit configured to generate stimulation information based on the audio signals received from the pre-processing unit, and a stimulator unit configured to generate stimulation signals based on the stimulation information. The hearing prosthesis also comprises a stimulation module configured to deliver the stimulation signals to a recipient.

17 Claims, 7 Drawing Sheets

(56) References Cited

U.S. PATENT DOCUMENTS

2006/0052841 A1* 3/2006 Daly .................. A61N 1/08
    607/57
2007/0147418 A1  6/2007 Son et al.
2010/0310084 A1* 12/2010 Hersbach ............ H04R 25/453
    381/71.6

OTHER PUBLICATIONS

Rejection Decision in Chinese Application No. 200980141013.8, dated Oct. 25, 2013, 9 pages.
European Examination Report in corresponding EP Application No. 09821198.0, dated Oct. 10, 2017, 5 pages.

* cited by examiner

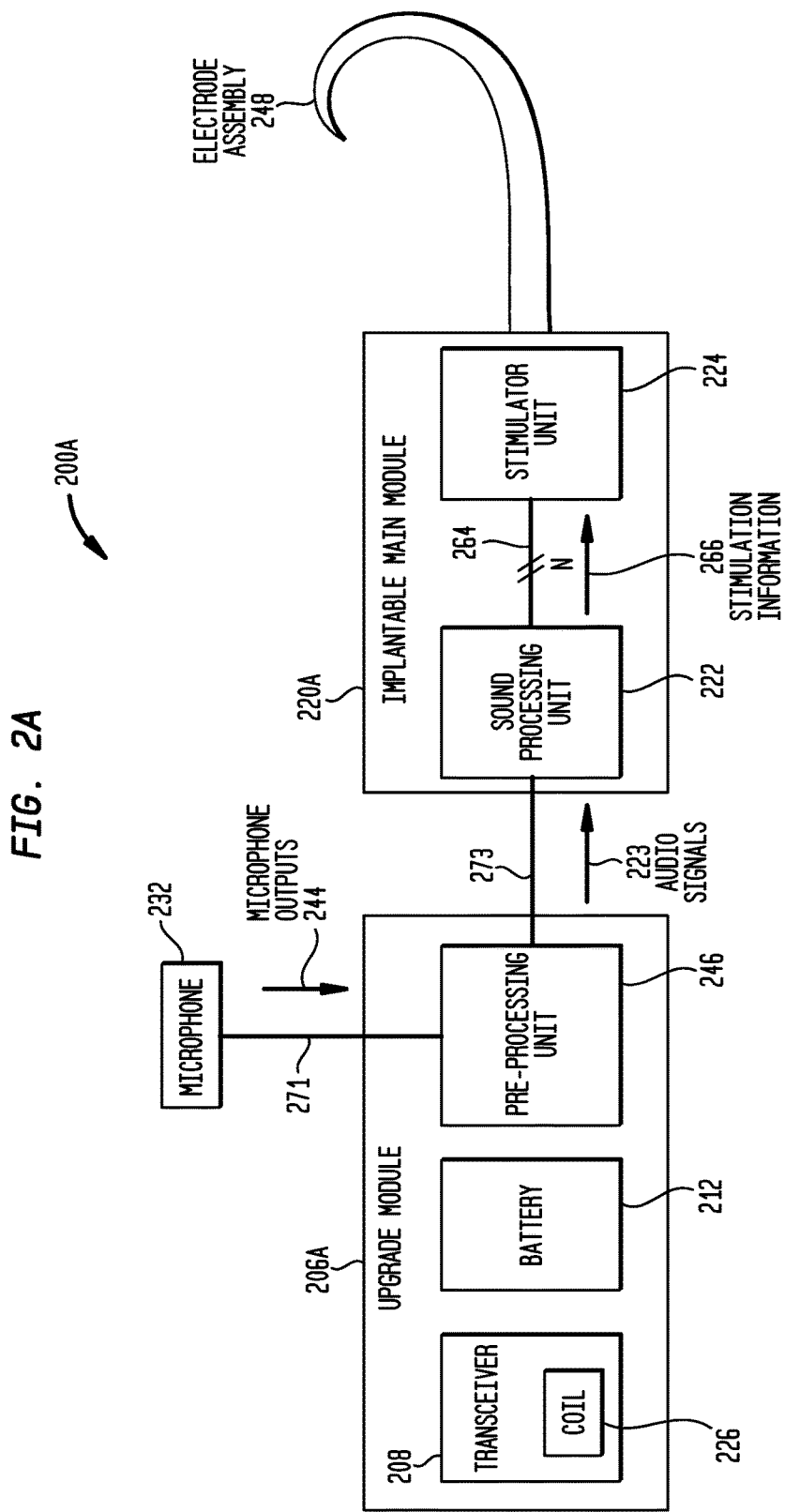

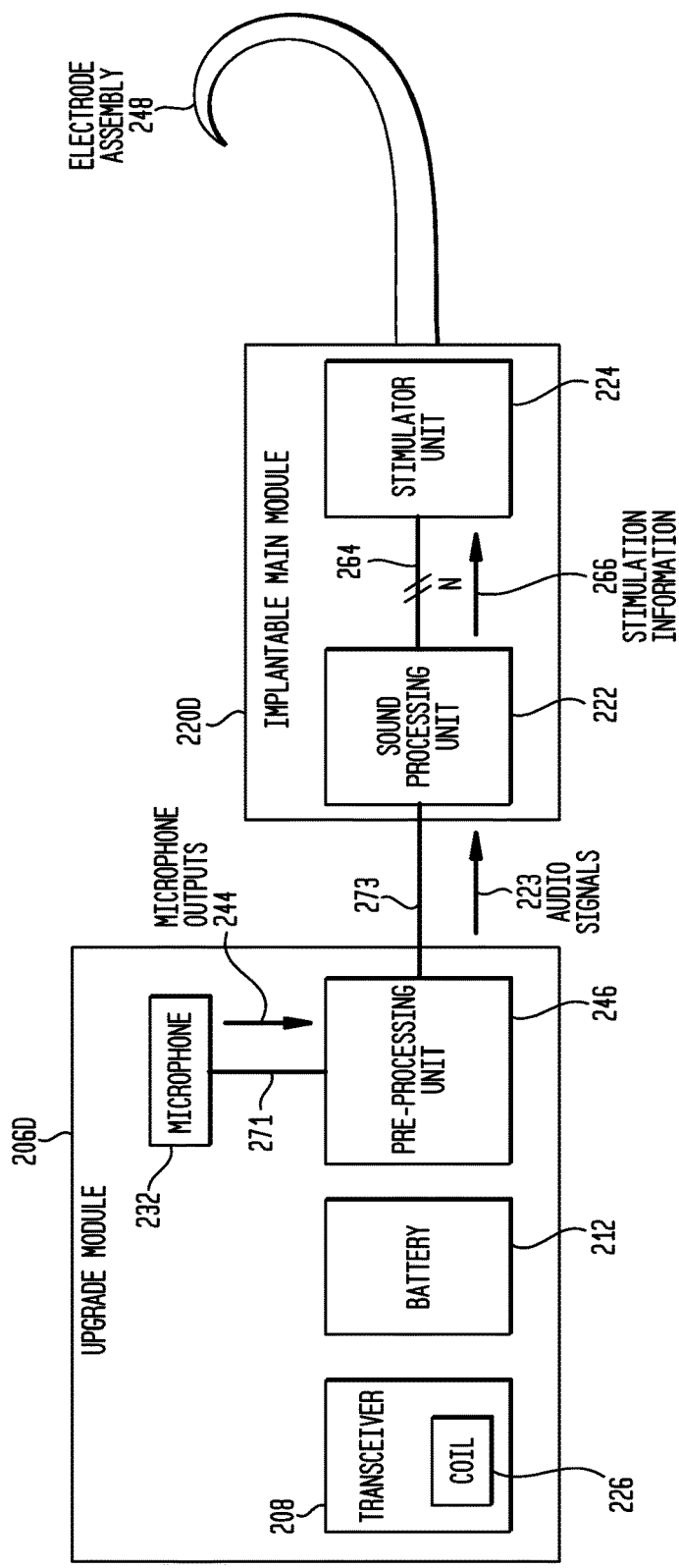

IMPLANTABLE HEARING PROSTHESIS

CROSS-REFERENCE TO RELATED APPLICATIONS

This application is a Continuation Application of U.S. application Ser. No. 13/124,047 filed Jul. 13, 2011, which is related to National Stage Application of International Application No. PCT/US2009/060676, filed Oct. 14, 2009, and claims the benefit of U.S. Provisional Application No. 61/105,406, filed Oct. 14, 2008. The contents of these applications are hereby incorporated by reference herein.

BACKGROUND

Field of the Invention

The present invention relates generally to a hearing prosthesis, and, more particularly, to an implantable hearing prosthesis.

Related Art

Medical devices having one or more implantable components, generally referred to as implantable medical devices, have provided a wide range of therapeutic benefits to patients over recent decades. One type of implantable medical device, implantable hearing prostheses, are widely used today.

Hearing loss, which may be due to many different causes, is generally of two types, conductive and sensorineural. In some cases, a person suffers from hearing loss of both types. Conductive hearing loss occurs when the normal mechanical pathway that sound travels to reach the cochlea is impeded, for example, by damage to the ossicles. Individuals suffering from conductive hearing loss typically have some form of residual hearing because the hair cells in the cochlea are undamaged. As a result, individuals suffering from conductive hearing loss typically receive an acoustic hearing aid, middle ear implant, or other implantable hearing prosthesis that provides acoustic or mechanical stimulation to generate mechanical motion of the cochlea fluid.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from hearing prostheses that generate mechanical motion of the cochlea fluid. Such individuals may benefit from implantable hearing prostheses that deliver electrical stimulation to nerve cells of the recipient's auditory system. As used herein, a recipient's auditory system includes all sensory system components used to perceive a sound signal, such as hearing sensation receptors, neural pathways, including the auditory nerve and spiral ganglion, and the regions of the brain used to sense sounds. Electrically-stimulating hearing prostheses include, but are not limited to, auditory brain stimulators and cochlear implants.

Cochlear implants are often proposed when the sensorineural hearing loss is due to the absence or destruction of the cochlear hair cells which transduce acoustic signals into nerve impulses. Cochlear implants generally include a stimulating assembly implanted in the cochlea to deliver electrical stimulation signals to the auditory nerve cells, thereby bypassing absent or defective hair cells. The electrodes of the stimulating assembly differentially activate auditory neurons that normally encode differential pitches of sound.

Auditory brain stimulators are often proposed to treat a smaller number of individuals with bilateral degeneration of the auditory nerve. For such recipients, an auditory brain stimulator provides stimulation of the cochlear nucleus in the brainstem.

Totally or fully implantable forms of the above and other implantable hearing prostheses have been developed to treat a recipient's conductive, sensorineural and/or combination hearing loss. As used herein, a totally implantable hearing prosthesis refers to a device in which all of the components of the device are implanted subcutaneously; that is there are no external components. One exemplary totally implantable cochlear implant is described in greater detail in U.S. Pat. No. 7,346,397, which is hereby incorporated by reference herein.

SUMMARY

In one aspect of the present invention a totally implantable hearing prosthesis is provided. The implantable hearing prosthesis comprises: an implantable microphone configured to receive sound signals and to output microphone information; an implantable upgrade module including a pre-processing unit configured to convert the microphone information into audio signals; a implantable main module, physically separate from and electrically connected to the upgrade module, comprising: a sound processing unit configured to convert the audio signals received from pre-processing unit into stimulation information, and a stimulator unit configured to generate stimulation signals based on the stimulation information; and a stimulation module configured to deliver the stimulation signals to a recipient.

In another aspect of the present invention an implantable hearing prosthesis is provided. The implantable hearing prosthesis comprises: a microphone configured to receive sound signals and to output microphone information; an implantable upgrade module including a pre-processing unit configured to convert the microphone information received from the microphone into audio signals; a implantable main module, physically separate from and electrically connected to the upgrade module, comprising: a sound processing unit configured to convert the audio signals received from the pre-processing unit into electrical stimulation information, and a stimulator unit configured to generate electrical stimulation signals based on the stimulation information; and an electrode assembly configured to deliver the stimulation signals to the recipient.

In a still other aspect of the present invention, a method of converting an acoustic sounds signal into a hearing percept is provided. The method comprises: receiving sound signals with an implanted microphone; converting, with a pre-processing unit positioned in an implantable upgrade module, microphone information received from the implanted microphone into audio signals; providing the audio signals to a sound processing unit positioned in a implantable main module which is physically separate from and electrically connected to the upgrade module; converting, with the sound processing unit, the audio signals into stimulation information; generating, with a stimulator unit positioned in the implantable main module, stimulation signals based on the stimulation information; and delivering the stimulation signals to a recipient with an implantable stimulation module.

BRIEF DESCRIPTION OF THE DRAWINGS

Embodiments of the present invention are described below with reference to the attached drawings, in which:

FIG. 2A is a block diagram of a cochlear implant in accordance with embodiments of the present invention;

FIG. 2D is a block diagram of a cochlear implant in accordance with embodiments of the present invention;

DETAILED DESCRIPTION

Aspects of the present invention are generally directed to a totally implantable hearing prosthesis having two or more physically separate and electrically connected implantable components. Specifically, the prosthesis comprises an implantable upgrade module, and a implantable main module that is physically separate from, and electrically connected to the upgrade module. The upgrade module comprises a rechargeable power source, and a pre-processing unit which performs microphone pre-processing on information received from a microphone. The pre-processed microphone information, referred to herein as audio signals, are provided to the implantable main module. The implantable main module comprises a sound processing unit that converts the audio signals into electrical stimulation information, and a implantable main module to generate stimulation signals based on the electrical stimulation information. The generated stimulations signals are delivered to the recipient via an implanted stimulation module.

Embodiments of the present invention are described herein primarily in connection with one type of implantable hearing prosthesis, namely a totally or fully implantable cochlear prosthesis (commonly referred to as a cochlear prosthetic device, cochlear implant, cochlear device, and the like; simply "cochlear implants" herein). As used herein, a totally implantable cochlear implant refers to an implant in which all components are implanted subcutaneously; that is under a recipient's skin or tissue. As such, a totally implantable cochlear implant is capable of operating, at least for a finite period of time, without the need for any external device.

It be appreciated that embodiments of the present invention are not limited to totally hearing prosthesis and may be implemented in any implantable hearing prosthesis now known or later developed. For example, embodiments of the present invention may be implemented in partially or mostly implantable cochlear implants, auditory brain stimulators, middle ear mechanical stimulators, hybrid electro-acoustic prosthesis or other prosthesis that electrically, acoustically and/or mechanically stimulate components of the recipient's outer, middle or inner ear.

Figure 1:
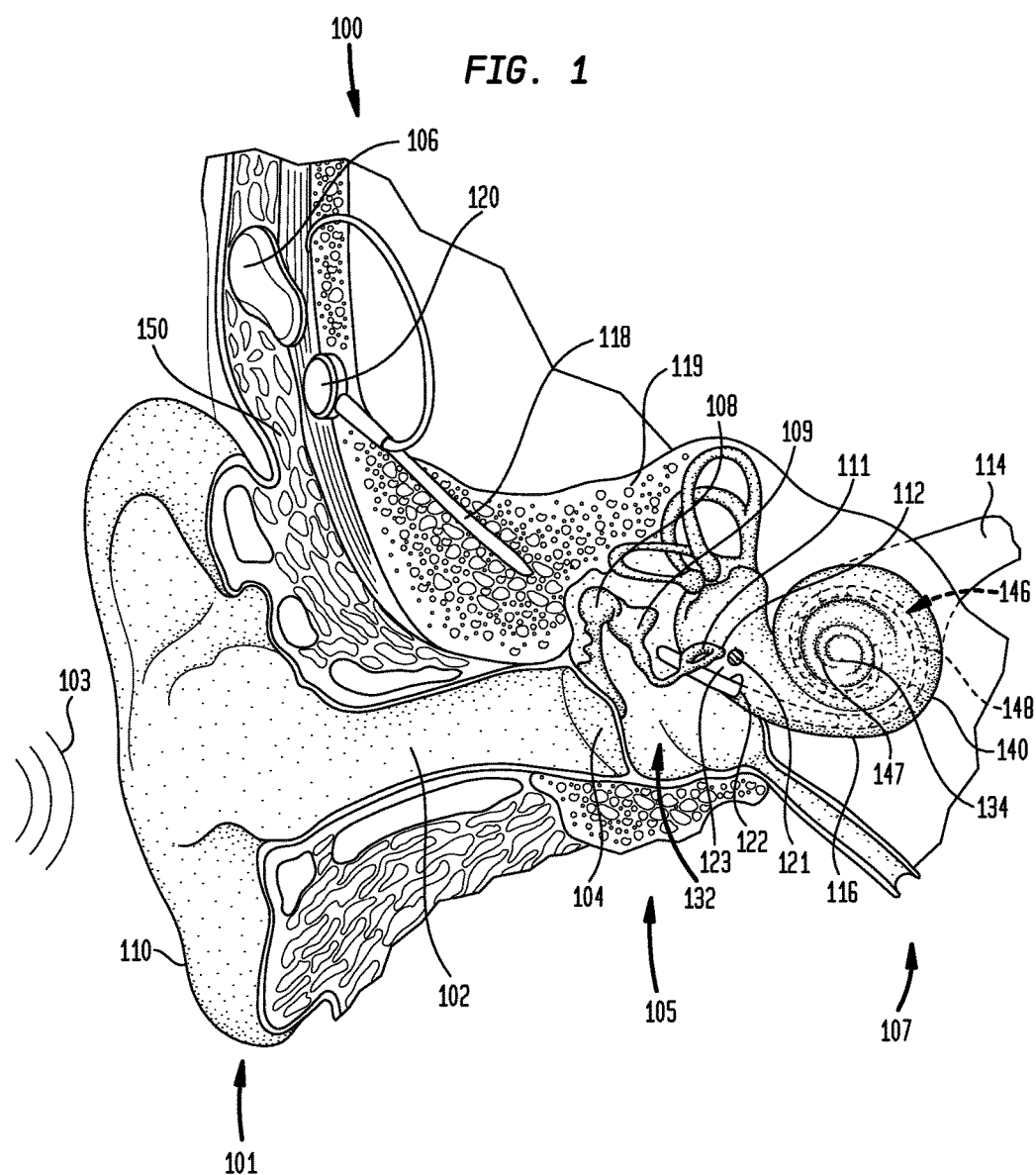
FIG. 1 is a perspective view of an exemplary totally implantable cochlear implant, in which embodiments of the present invention may be implemented.

FIG. 1 is perspective view of a totally implantable cochlear implant 100 in accordance with embodiments of the present invention. Cochlear implant 100 is shown implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 132 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises microphone (not shown) configured to be implanted under the recipient's skin/tissue 150, and to receive sound signals, and two or more physically separate and electrically connected components implanted in the recipient. Specifically, cochlear implant 100 comprises an upgrade module 106 that provides an upgrade path for a rechargeable power source disposed therein. As described in greater detail below, upgrade module 106 also comprises a pre-processing module (not shown) to perform microphone pre-processing and to provide audio signals to implantable main module 120 Microphone pre-processing refers to the conversion of microphone information, such as sound pressure, acceleration, velocity, etc., into audio signals containing information in the hearing range (i.e. approximately 20 HZ to 20 kHz) representing sound signals detected by the microphone.

As noted, an implantable microphone detects sound waves, sometimes referred to herein as sound signals. An implanted microphone may be sensitive to both air-borne sound (sometimes referred to herein as air-conducted sounds) as well as body or bone-borne sound (sometimes referred to herein as body-noises). However, generally only the air-conducted sounds are useful in evaluating a desired or target acoustic sound signals originating externally to the recipient, and the body-noise typically comprises noise that degrades performance of the microphone. For example, body-noise, such as breathing, chewing, muscle movements, speaking, etc. may be conducted through the recipient's skull to the implanted microphone. The body-noise detected by the microphone may have an amplitude which is the same, or greater than the amplitude of a concurrently-received air-conducted sound. In such situations, the implanted microphone detects both the desired air-conducted sound as well as the bone-conducted noise, and the hearing prosthesis is unable to differential between the sounds.

In certain embodiments, the microphone pre-processing within upgrade module 106 is used to reduce or suppress body-noise detected by the microphone. In such embodiments, the audio signals output by the pre-processing unit comprise electrical representations of the received sounds signals from which body-noises have been substantially removed. For example, in embodiments of the present invention in which the microphone is a single subcutaneous microphone, the microphone pre-processing implements one or more algorithms or other processing techniques to directly suppress received body-noise from the received sound signals. In other embodiments, the microphone comprises a two element subcutaneous microphone having, for example, a first element that detects sound signals, and an accelerometer which detects movement of the recipient's skull. In such embodiments, the microphone pre-processing combines the detected sound signals and the output of the accelerometer to so as to suppress bone conducted sound detected by the first element of the microphone. In still other embodiments, cochlear implant 100 comprises two or more microphones implanted in the recipient. In these embodiments, the microphone pre-processing combines the microphone information from the two or microphones in manner so as to substantially eliminate bone conducted sound.

It would be appreciated that a number of different microphones and microphone configurations may be utilized in embodiments of the present invention. Therefore, the microphone pre-processing may be modified to eliminate bone conducted sound utilizing different techniques depending on the type of microphone implanted, the microphone position, number of microphones, etc.

As described below, the implantable microphone may be at least partially positioned in upgrade module 106, or may be positioned elsewhere in the recipient. Also as described in greater detail below, in certain embodiments, upgrade module 106 may further comprise a receiver or transceiver unit configured to receive data and/or power signals from an external device (not shown).

Cochlear implant 100 further comprises a implantable main module 120 having a sound processing unit (not shown) for sound processing of audio signals provided from the pre-processing unit. As used herein, sound processing refers to the translation of the one or more audio signals output by the pre-processing unit into electrical stimulation information, such as electrode/current levels, or of the translation of the audio signals into mechanical/acoustic stimulation information. Implantable main module 120 further includes a stimulator unit (also not shown) which utilizes the electrical stimulation information provided by the sound processing unit to generate electrical stimulation signals which, when delivered to the recipient, evoke a hearing sensation of the audio signals.

The electrical stimulation signals generated by the stimulator unit are delivered to the recipient via elongate stimulating lead assembly 118. Elongate stimulating lead assembly 118 has a proximal end connected to implantable main module 120, and a distal end implanted in cochlea 140. Stimulating lead assembly 118 extends from implantable main module 120 to cochlea 140 through mastoid bone 119. In some embodiments stimulating lead assembly 118 may be implanted at least in basal region 116 of cochlea 140, and sometimes further. For example, stimulating lead assembly 118 may extend towards apical end of cochlea 140, referred to as cochlea apex 134. In certain circumstances, stimulating lead assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating lead assembly 118 comprises a longitudinally aligned and distally extending array 146 of electrodes 148, sometimes referred to as electrode array 146 herein, disposed along a length thereof. Although electrode array 146 may be disposed on stimulating lead assembly 118, in most practical applications, electrode array 146 is integrated into stimulating lead assembly 118. As such, electrode array 146 is referred to herein as being disposed in stimulating lead assembly 118. The stimulation signals generated by the stimulator unit are applied by electrodes 148 to cochlea 140, thereby stimulating auditory nerve 114.

As noted, cochlear implant 100 comprises a totally implantable prosthesis that is capable of operating, at least for a finite period of time, without the need for an external device. Therefore, cochlear implant 100 further comprises a rechargeable power source (not shown) located in upgrade module 106 that stores power received from an external device. The power source may comprise, for example, a rechargeable battery. During operation of cochlear implant 100, the power stored by the power source is distributed to the various other implanted components as needed.

As described in greater detail below, upgrade module 106 is physically separate from implantable main module 120, and attached electrode assembly 148. Due to this physical separation, upgrade module 106 may be removed from the recipient without disturbing the implanted location of electrode assembly 148. As such, this provides the ability to remove upgrade module 106 from the recipient via a relatively straightforward surgical procedure, thereby providing the ability to easily replace or upgrade the components of module 106 such as, for example, the power source positioned therein.

FIG. 2A is a block diagram of a totally implantable cochlear implant 200A in accordance with embodiments of the present invention. In the illustrative embodiments, cochlear implant 200A comprises an upgrade module 206A, a microphone 232, and a implantable main module 220A having an electrode assembly 248 extending there from. In the illustrative embodiments of FIG. 2A, upgrade module 206A and implantable main module 220A are physically separate, electrically connected components.

In the embodiments of FIG. 2A, microphone 232 is an implantable microphone 232 configured to detect sound signals. As such, because all components of cochlear implant 200A are configured to be implanted, cochlear implant 200A operates, for at least a finite period of time, without the need of an external device.

It should be appreciated that embodiments of the present invention may use any implantable microphone, and/or any microphone position, now know or later developed. For example, in certain embodiments, microphone 232 comprises a subcutaneous microphone, such as the microphone described in U.S. Pat. No. 6,093,144, which is hereby incorporated by reference herein. In certain embodiments, microphone 232 comprises a microphone implanted in the inner ear of the recipient, such as the microphone described in U.S. Pat. No. 5,782,744 and U.S. Patent Publication No. 2005/0177204, which are hereby incorporated by reference herein. In other embodiments, microphone 232 comprises a microphone implanted in the middle ear of the recipient, such as the microphone described in U.S. Provisional Patent Application No. 60/757,019, the contents of which is hereby incorporated by reference herein. In still other embodiments, microphone 232 may comprise a microphone implanted in or adjacent ear canal 102 of the recipient. For example, in one such embodiment, microphone 232 is substantially similar to the microphone described in U.S. Pat. No. 5,814,095, which is hereby incorporated by reference herein. It should also be appreciated that different positions/placements of microphone 232 are possible. For example, certain positions might be less sensitive to body-noises of the particular recipient.

Microphone 232 provides microphone information, such as sound pressure, acceleration, velocity, etc., to pre-processing unit 246 in upgrade module 206A via an electrical connection 271. This microphone information is shown in FIG. 2A as microphone outputs 244. In the embodiments of FIG. 2A, electrical connection 271 comprises a wire connection extending between microphone 232 and pre-processing unit 246.

Although FIG. 2A illustrates embodiments of the present invention utilizing an implantable microphone 232, it would be appreciated that in alternative embodiments, microphone 232 may be positioned externally to the recipient. In such embodiments, microphone outputs 244 may be transcutaneously transferred to pre-processing unit 246.

As noted above with reference to FIG. 1, pre-processing unit 246 performs microphone pre-processing; that is, the conversion of the microphone information such as acceleration, pressure, velocity, etc. into audio signals 223 representing the sound signals detected by microphone 232. Also as noted above, in certain embodiments, pre-processing unit 246 is used to reduce or suppress body-noise detected by microphone 232. Thus, in such embodiments audio signals 223 comprise electrical representations of the received sound signals from which body-noise have been substantially removed. For example, in embodiments of the present invention in which microphone 232 is a single subcutaneous microphone, the pre-processing unit 246 directly suppresses received body-noise from the received acoustic signals. In other embodiments, microphone 232 comprises a two element subcutaneous microphone having, for example, a first element that detects acoustic sound signals, and an accelerometer which detects movement of the recipient's skull. In such embodiments, pre-processing unit 246 combines the detected acoustic sound signals and the output of the accelerometer to so as to suppress bone conducted sound detected by the first element of the microphone. In still other embodiments, cochlear implant comprises two or more microphones implanted in the recipient. In these embodiments, pre-processing unit 246 combines the microphone information from the two or microphones in manner so as to substantially eliminate bone conducted sound.

As noted, a number of different microphones and microphone configurations may be utilized in embodiments of the present invention. Therefore, the microphone pre-processing may be modified to eliminate bone conducted sound utilizing different techniques depending on the type of microphone implanted, the microphone position, number of microphones, etc.

Audio signals 223 are delivered to sound processing unit 222 in implantable main module 220A via electrical connection 273. Because signals 223 are audio signals, a small number of electrical pathways may be used to provide the signals to sound processing unit 222. As such, in certain embodiments, electrical connection 273 comprises a single wire extending between pre-processing unit 246 and sound processing unit 222. In alternative embodiments, electrical connection 273 comprises two wires extending between pre-processing unit 246 and sound processing unit 222.

Embodiments of the present invention capitalize on the relatively small bandwidth required to transfer audio signals 223. Such audio signals require a data transfer rate of approximately 64 Kb/s. The inventors of the present application observed that in contrast, the current and anticipated future sound coding strategies that are or may be implemented in sound processing unit 222 require or will require a data transfer rate of at least 40 Mb/s, which is expected to increase dramatically in the near future. As data rates increase, the problems of timing, power consumption, electromagnetic interference, crosstalk etc., across system connections become more problematic. Conventional solutions for transferring the data in a hearing prosthesis in which the sound processing unit and stimulating unit are both implanted in a recipient is to implement a hardware/software scheme in upgrade module 206A and main module 220A to provide a reliable digital data communications protocol to transfer such data over electrical connection 273 between implanted modules. And, future sound coding strategies, which will be of greater complexity and require greater data transfer rates, will require incremental enhancements to the implemented architecture which will increase the power required to transfer data.

In contrast to such conventional approaches, the inventors altered the system architecture, placing sound processing unit 222 in the same module as the stimulator unit 224, and segregated the pre-processing components of sound processing unit 222 and placing such components in upgrade module 206A. By doing so, audio signals 223 are transferred from upgrade module 206A to speech processing unit 222, and stimulation information/data 266 is transferred from sound processing unit 222 to stimulator unit 224 This approach eliminates the need to implement digital data communications protocol as noted above. Rather, audio signals 223 may be transferred from pre-processing unit 246 to sound processing unit 222 via any simple technique over a minimal quantity of conductors. Further, stimulation data 266 may be transferred from sound processing unit 222 to stimulator unit 224 using any of a myriad of techniques now or later developed to transfer data between system components, such as via one or more data buses and/or via memory. Exemplary usable data buses include parallel buses, which carry data words in parallel on multiple wires, or serial buses, which carry data in bit-serial form.

In addition to the above, the architecture of the present invention facilitates future growth. For example, the audio interface implemented in sound processing unit 222 to receive audio signals 223 from pre-processing unit 246 facilitates the replacement of upgrade module 206A over time since the audio interface may be a well-known standard interface. Furthermore, the internal system interfaces, such as the buses described above, provided to transfer data from sound processing unit 222 to stimulator unit 224 may easily support increases in the data transfer rate due to, for example, implementation of more complex sound coding strategies, an increase in stimulation channels, etc.

Sound processing unit 222 implements one or more sound coding strategies to translate audio signals 223 output by pre-processing unit 246 into electrical stimulation information 266, such as electrode/current levels. Electrical stimulation information 266 is provided to stimulator unit 244 via electrical connections 264 and is used by stimulator unit 224 to generate electrical stimulation signals for delivery to the recipient via electrode assembly 248. It should be appreciated that there are several coding strategies that may be implemented by sound processing unit 222 to convert audio signals 223 into electrical stimulation information. Embodiments of the present invention may be used in combination with any sound processing strategy now or later developed, including but not limited to Continuous Interleaved Sampling (CIS™), Spectral PEAK Extraction (SPEAK™), Advanced Combination Encoders (ACE™), Simultaneous Analog Stimulation (SAS), MPS, Paired Pulsatile Sampler (PPS), Quadruple Pulsatile Sampler (QPS), Hybrid Analog Pulsatile (HAPs), n-of-m and HiRes®, developed by Advanced Bionics. SPEAK™ is a low rate strategy that may operate within the 250-500 Hz range. ACE™ is a combination of CIS™ and SPEAK™. Examples of such strategies are described in U.S. Pat. No. 5,271,397, the entire contents and disclosures of which is hereby incorporated by reference. (HiRes is a registered trademark of Advanced Bionics Corporation, Sylmar, Calif., USA. SPEAK, ACE, and CIS are trademarks of Cochlear Limited, Lane Cove, NSW, Australia).

In the illustrative embodiment of FIG. 2A, upgrade module 206A is physically separate from microphone 232 and implantable main module 220A. However, upgrade module 206A is electrically connected to microphone 232 and implantable main module 220A. As such, cochlear implant 200A comprises three separate electrically connected components implantable in the recipient.

As noted above, FIG. 2A illustrates embodiments of the present invention in which microphone 232 and modules 206A and 220A are connected to one another by a physical connectors in the form of wires. It would be appreciated that microphone 232 and modules 206A and 220A may be electrically connected to one another in any manner now know or later developed. For example, in embodiments in which a physical connection is used, a connector may be disposed between the modules to facilitate disconnection of the modules from one another, thereby permitting removal of one module without necessitating the removal of other modules. In other embodiments, wireless connections may be used to electrically couple microphone 232 and modules 206A and 220A to one another. For ease of illustration, some of the wireless connections between components of the modules, as well as the connections between different modules have been omitted.

As noted above, in embodiments of the present invention, pre-processing unit 246 in upgrade module 206A provides audio signals 223 to sound processing unit 222. In embodiments in which a physical connection is used between upgrade module 206A and implantable main module 220A, the physical connection comprises a relatively small number of connections (i.e. 2-4 wires). This small number of connections is possible because the audio signals may be transferred over one or two wires, and the only additional wires are utilized for the transmission of power and/or additional data.

Also as noted, upgrade module 206A includes a power source 212 which provides power to the components of upgrade module 206A, implantable main module 220, and microphone. Power is delivered to the components of upgrade module 206A, as well as microphone 232 and implantable main module 220 via the electrical connections described above. In certain embodiments, power source 212 comprises a rechargeable power source, such as a rechargeable battery 212.

Conventional batteries suitable for implantation in recipient to not have an infinite operational life, and often need to be replaced (e.g. every 5-10 years). As noted above, in embodiments of the present invention, battery 212 is positioned in upgrade module 206A which is physically separate from implantable main module 220A and attached electrode assembly 248. Furthermore, because, as noted, upgrade module 206A provides audio signals 223 to implantable main module 220A rather than stimulation signals, a relatively small number of connections between upgrade module 206A and implantable main module 220A may be used. The physical separation of modules 206A and 220A, combined with a small number of connections extending there between, allows the removal of upgrade module 206A from the recipient without disturbing the implanted location of electrode assembly 248. Thus, upgrade module 206A may be removed from the recipient via s relatively simple surgical procedure.

The ability to easily remove upgrade module 206A provides an upgrade or replacement pathway for battery 212 within the module. Thus, a recipient may be able to receive the newest battery technologies via a simple surgical procedure.

Additionally, embodiments of the present invention provide upgrade path for small children. As would be appreciated, due to limited space within the skull it may be difficult to initially implant a battery in a child or young adult. Thus, younger recipients may initially receive a cochlear implant comprising a implantable main module configured to receive power, acoustic sound signals, etc., from an external component. Through the use of embodiments of the present invention, such younger recipients may receive an upgrade module when there is sufficient room in the skull, thereby converting their conventional cochlear implant into a totally implantable cochlear implant.

As shown, microphone 232 is also physically separate from implantable main module 220A and attached electrode assembly 248. As such, microphone 232 may be removed from the recipient without disturbing electrode assembly 248, thereby providing the ability to upgrade or replace microphone 232 via a relatively straightforward surgical procedure.

As noted above, cochlear implant 200A is configured to operate, for at least a period of time, without an external device. However, it is sometimes desirable to communicate with an external device to, for example, recharge battery 212. As such, cochlear implant 200A also includes a receiver or transceiver 208 positioned in upgrade module 206A. Transceiver 208 has an internal coil 226 that receives power and/or data signals from an inductively coupled external device. Coil 226 acts as a data receiver or as a power receiver during recharging of battery 212. In some embodiments, the coil 226 is also used as a telemetry transmitter which provides a bidirectional interface between cochlear implant 200A and any external devices configured to communicate via an inductive link. Although cochlear implant 200A is described herein with reference to the use of transceiver 208, it would be appreciated that in other embodiments any or all components of cochlear implant 200A may have the capability to communicate with an external device when necessary, particularly for program upgrades and/or implant interrogation, and to modify the operating parameters of the device.

It would be appreciated that upgrade module 206A may also comprise one or more other electronic components for controlling the operation of cochlear implant 200A, or for controlling any specific components of cochlear implant 200A. For ease of illustrations, these additional electronic components have been omitted from FIG. 2A.

Figure 2B:
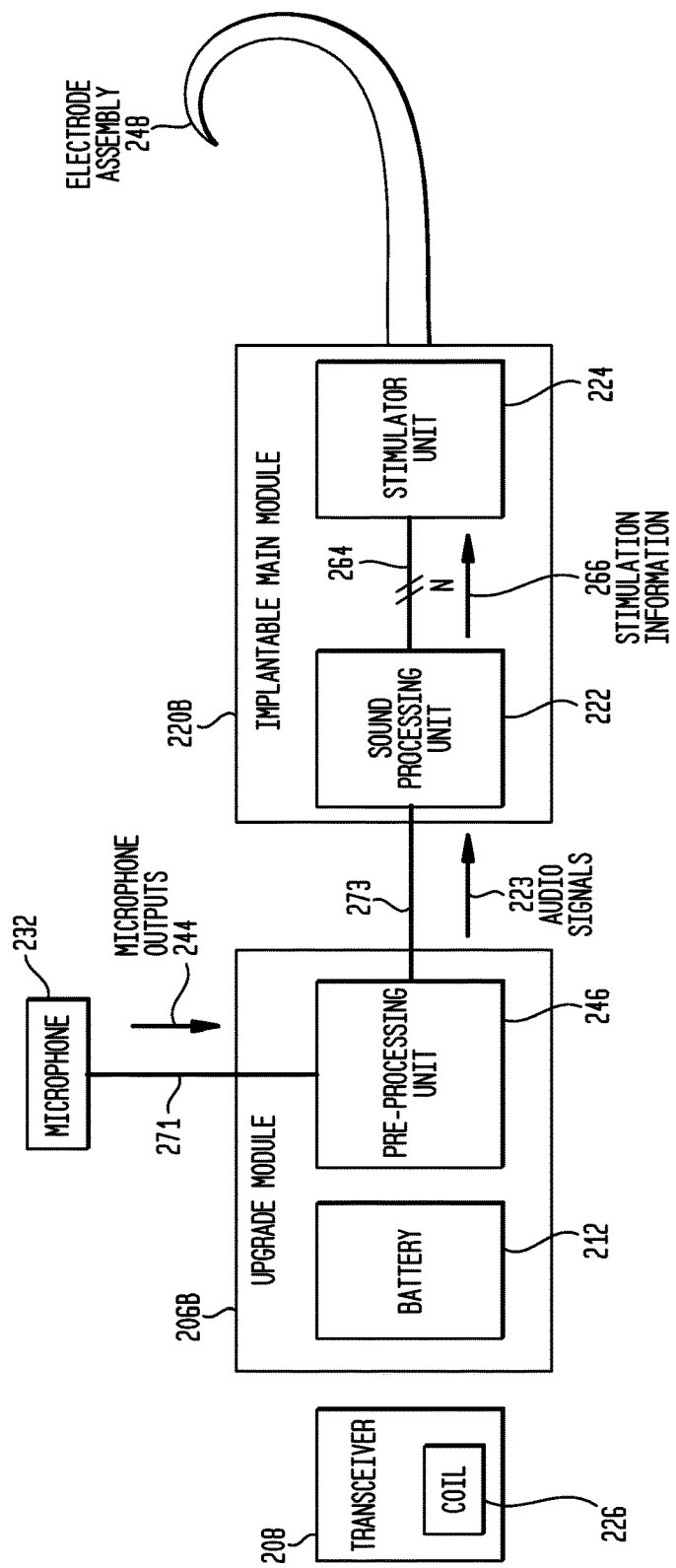
FIG. 2B is a block diagram of a cochlear implant in accordance with embodiments of the present invention.

FIG. 2B is a block diagram of a cochlear implant 200B in accordance with further embodiments of the present invention. Similar to the embodiments of FIG. 2A, cochlear implant 200B comprises an implantable upgrade module 206B, a microphone 232, and a implantable main module 220B having an electrode assembly 248 extending there from. In the illustrative embodiments of FIG. 2B, upgrade module 206B and implantable main module 220B are physically separate, electrically connected components.

As shown, cochlear implant 200B includes an implantable microphone 232 which receives sound signals, and provides microphone outputs 244 via electrical connection 271 to pre-processing unit 246 in upgrade module 206B. As detailed above, pre-processing unit 246 converts microphone outputs 244 into audio signals 223. These audio signals 223 are provided to sound processing unit 222 via electrical connection 273. Sound processing unit 222 implements one or more sound coding strategies to translate audio signals 223 output by pre-processing unit 246 into electrical stimulation information 266, such as electrode/current levels. Electrical stimulation information 266 is provided to stimulator unit 244 via electrical connections 264 and is used by stimulator unit 224 to generate electrical stimulation signals for delivery to the recipient via electrode assembly 248.

Although FIG. 2B illustrates embodiments of the present invention utilizing an implantable microphone 232, it would be appreciated that in alternative embodiments, microphone 232 may be positioned externally to the recipient. In such embodiments, microphone outputs 244 may be transcutaneously transferred to pre-processing unit 246.

In the embodiments of FIG. 2B, upgrade module 206B also includes a power source 212, shown as battery 212. It would be appreciated that upgrade module 206B may also comprise one or more other electronic components for controlling the operation of cochlear implant 200B, or for controlling any specific components of cochlear implant 200B. For ease of illustrations, these additional electronic components have been omitted from FIG. 2B.

Similar to the embodiments of FIG. 2A, cochlear implant 200B is configured to operate, for at least a period of time, without an external device. However, it is sometimes desirable to communicate with an external device to, for example, recharge battery 212. As such, cochlear implant 200B also includes a receiver or transceiver 208 which has an internal coil 226 that receives power and/or data signals from an inductively coupled external device. In some embodiments, the coil 226 is also used as a telemetry transmitter which provides a bidirectional interface between cochlear implant 200B and any external devices configured to communicate via an inductive link. Although cochlear implant 200B is described herein with reference to the use of transceiver 208, it would be appreciated that in other embodiments any or all components of cochlear implant 200B may have the capability to communicate with an external device when necessary, particularly for program upgrades and/or implant interrogation, and to modify the operating parameters of the device.

In the illustrative embodiments of FIG. 2B, transceiver 208 is physically separate from, but electrically connected to upgrade module 206B. As noted above, microphone 232 and modules 206B and 220B are also physically separate from one another. As such, cochlear implant 200B comprises four separate electrically connected components implantable in the recipient. Similar to the embodiments of FIG. 2A, upgrade module 206B may be electrically connected to transceiver 208, microphone 232 and implantable main module 220B in any manner now know or later developed. For example, upgrade module 206B may be electrically connected to each of transceiver 208, microphone 232 and implantable main module 220B via a physical connection, as noted above, or via a wireless connection. In embodiments in which a physical connection is used, a connector may be disposed between the modules to facilitate disconnection of the modules from one another, thereby permitting removal of one module or component without necessitating the removal of other modules. For ease of illustration, some of the wireless connections between components of the modules, as well as the connections between different modules have been omitted.

Figure 2C:
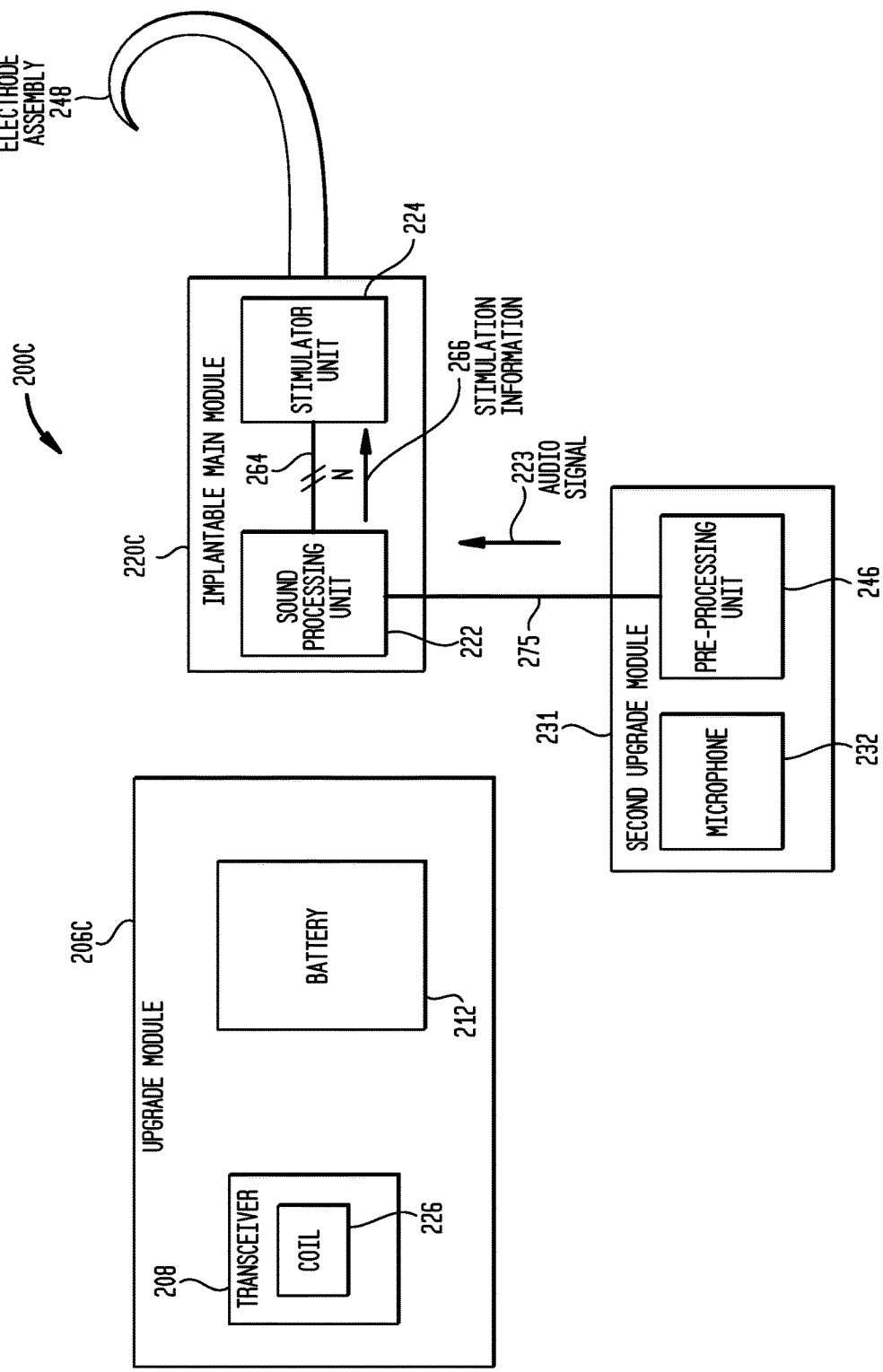
FIG. 2C is a block diagram of a cochlear implant in accordance with embodiments of the present invention.

FIG. 2C is a block diagram of a totally implantable cochlear implant 200C in accordance with further embodiments of the present invention. Cochlear implant 200C comprises an implantable upgrade module 206C, an implantable second upgrade module 231, and a implantable main module 220C having electrode assembly 248 extending there from. In the illustrative embodiments of FIG. 2C, second upgrade module 231, upgrade module 206C and implantable main module 220C are physically separate, electrically connected components.

As shown, second upgrade module 231 includes an implantable microphone 232 which receives sound signals. Second upgrade module 231 further comprises a pre-processing unit 246. As detailed above, pre-processing unit 246 converts microphone outputs (not shown) into audio signals 223 that are provided to sound processing unit 222 in implantable main module 220C. As shown in FIG. 2C, audio signals 223 are provided to sound processing unit 222 via electrical connection 275. Sound processing unit 222 implements one or more sound coding strategies to translate audio signals 223 output by pre-processing unit 246 into electrical stimulation information 266, such as electrode/current levels. Electrical stimulation information 266 is provided to stimulator unit 244 via electrical connections 264 and is used by stimulator unit 224 to generate electrical stimulation signals for delivery to the recipient via electrode assembly 248.

In the embodiments of FIG. 2C, upgrade module 206C includes a power source 212, shown as battery 212. It would be appreciated that upgrade module 206C may also comprise one or more other electronic components for controlling the operation of cochlear implant 200C, or for controlling any specific components of cochlear implant 200C. For ease of illustrations, these additional electronic components have been omitted from FIG. 2C.

Similar to the embodiments of FIG. 2A, cochlear implant 200C is configured to operate, for at least a period of time, without an external device. However, it is sometimes desirable to communicate with an external device to, for example, recharge battery 212. As such, upgrade module 206C has positioned therein transceiver 208 which has an internal coil 226 that receives power and/or data signals from an inductively coupled external device. In some embodiments, coil 226 is also used as a telemetry transmitter which provides a bidirectional interface between cochlear implant 200C and any external devices configured to communicate via an inductive link. Although cochlear implant 200C is described herein with reference to the use of transceiver 208, it would be appreciated that in other embodiments any or all components of cochlear implant 200C may have the capability to communicate with an external device when necessary, particularly for program upgrades and/or implant interrogation, and to modify the operating parameters of the device.

As noted above, modules 206C, 231 and 220C are physically separate one another. As such, cochlear implant 200C comprises three separate electrically connected components implantable in the recipient. Similar to the embodiments of FIG. 2A, upgrade module 206C may be electrically connected to second upgrade module 231 and implantable main module 220C in any manner now know or later developed. For example, upgrade module 206C may be electrically connected to each of second upgrade module 231 and implantable main module 220C via a physical connection, or via a wireless connection. In embodiments in which a physical connection is used, a connector may be disposed between the modules to facilitate disconnection of the modules from one another, thereby permitting removal of one module or component without necessitating the removal of other modules. For ease of illustration, some of the wireless connections between components of the modules, as well as the connections between different modules have been omitted.

FIG. 2D is a block diagram of a totally implantable cochlear implant 200D in accordance with further embodiments of the present invention. Cochlear implant 200D comprises an implantable upgrade module 206D and a implantable main module 220D having electrode assembly 248 extending there from. In the illustrative embodiments of FIG. 2D, upgrade module 206D and implantable main module 220D are physically separate, electrically connected components.

As shown, upgrade module 206D has an implantable microphone 232 at least partially positioned therein. Microphone 232 receives sound signals, and provides microphone outputs 244 to pre-processing unit 246 via electrical connection 271. As detailed above, pre-processing unit 246 converts microphone outputs 244 into audio signals 223 that are provided to sound processing unit 222 via electrical connection 273. Sound processing unit 222 implements one or more sound coding strategies to translate audio signals 223 output by pre-processing unit 246 into electrical stimulation information 266, such as electrode/current levels. Electrical stimulation information 266 is provided to stimulator unit 244 via electrical connections 264 and is used by stimulator unit 224 to generate electrical stimulation signals for delivery to the recipient via electrode assembly 248.

In the embodiments of FIG. 2D, upgrade module 206D also includes a power source 212, shown as battery 212. It would be appreciated that upgrade module 206D may also comprise one or more other electronic components for controlling the operation of cochlear implant 200D, or for controlling any specific components of cochlear implant 200D. For ease of illustrations, these additional electronic components have been omitted from FIG. 2D.

Similar to the embodiments of FIG. 2A, cochlear implant 200D is configured to operate, for at least a period of time, without an external device. However, it is sometimes desirable to communicate with an external device to, for example, recharge battery 212. As such, upgrade module 206D also includes a transceiver 208 which has an internal coil 226 that receives power and/or data signals from an inductively coupled external device. In some embodiments, the coil 226 is also used as a telemetry transmitter which provides a bidirectional interface between cochlear implant 200D and any external devices configured to communicate via an inductive link. Although cochlear implant 200D is described herein with reference to the use of transceiver 208, it would be appreciated that in other embodiments any or all components of cochlear implant 200D may have the capability to communicate with an external device when necessary, particularly for program upgrades and/or implant interrogation, and to modify the operating parameters of the device.

As noted, in the illustrative embodiments of FIG. 2D, upgrade module 206D is physically separate from implantable main module 220D. As such, cochlear implant 200D comprises two separate electrically connected components implantable in the recipient. Similar to the embodiments of FIG. 2A, upgrade module 206D may be electrically connected to and implantable main module 220D in any manner now know or later developed. For example, upgrade module 206D may be electrically connected to implantable main module 220D via a physical connection, or via a wireless connection. In embodiments in which a physical connection is used, a connector may be disposed between the modules to facilitate disconnection of the modules from one another, thereby permitting removal of one module or component without necessitating the removal of other modules. For ease of illustration, some of the wireless connections between components of the modules, as well as the connections between different modules have been omitted.

As explained above, embodiments of the present invention may be used in conjunction with any cochlear implant or implantable hearing prosthesis now known or developed. For example, embodiments of the present invention may be used in hearing prosthesis that do not electrically stimulate the recipient, such as any prosthesis that acoustically and/or mechanically stimulates the middle or inner ear of the recipient. In such embodiments, a implantable main module may include the appropriate hardware and/or software to generate and output the necessary stimulation signals for use with the acoustic and/or mechanical actuator.

Likewise, as noted above, in certain embodiments of the present invention a cochlear implant may be configured to generate and deliver both electrical and acoustic (or mechanical) stimulation signals to a recipient. Such a cochlear implant, sometimes referred to as a hybrid, bimodal or multimodal cochlear implant (collectively bimodal cochlear implant herein), may be implanted in accordance with any of the embodiments of described above with reference to FIGS. 2A-2D. It would be appreciated that various necessary or desired hardware and/or software changes would be within the scope of the present invention.

Figure 3:
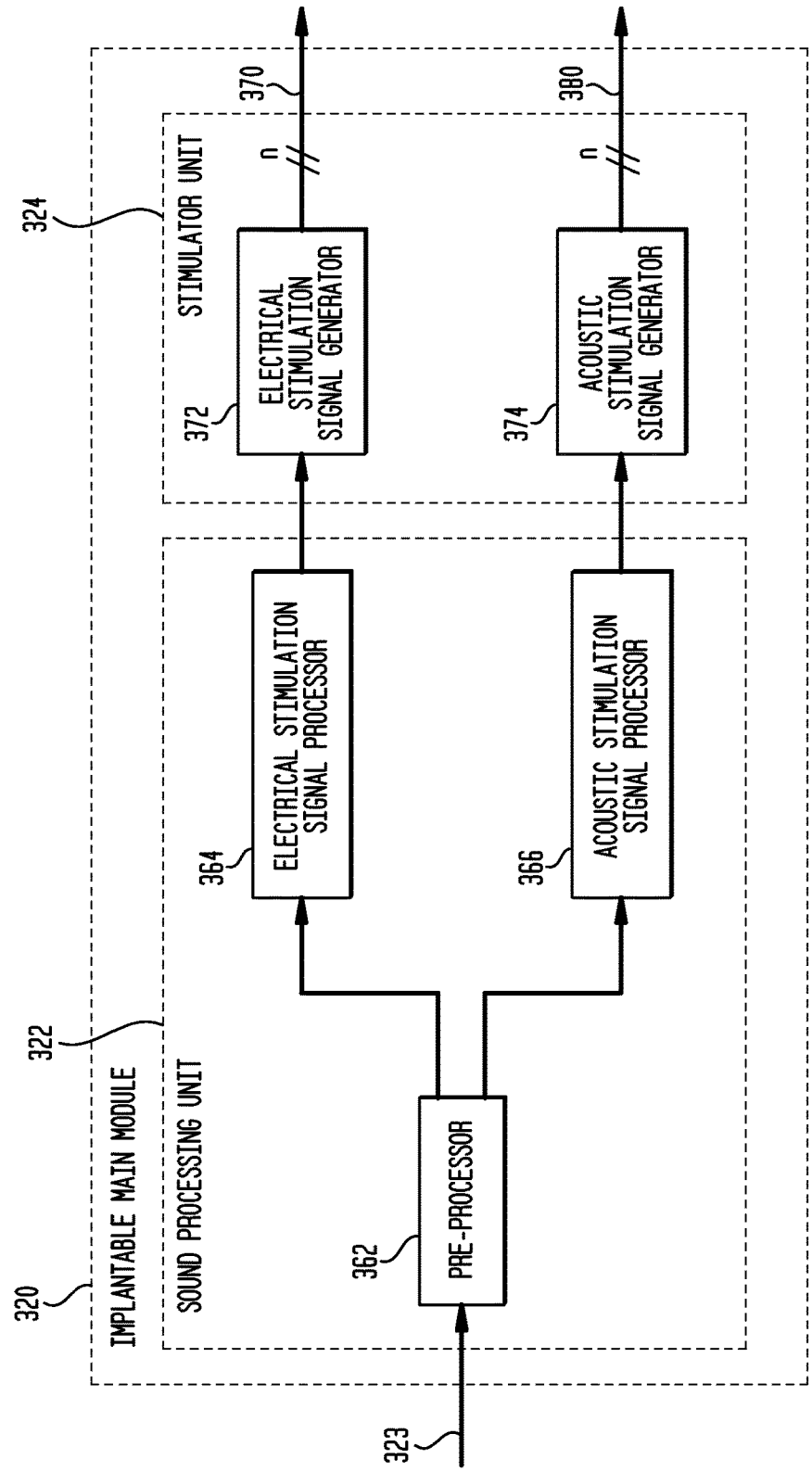
FIG. 3 is a functional block diagram of a implantable main module utilized in a bimodal hearing prosthesis in accordance with embodiments of the present invention.

FIG. 3 illustrates one specific embodiment of a implantable main module 320 which may be utilized in a bimodal cochlear implant in accordance with embodiments of the present invention. In the illustrative embodiment, implantable main module comprises a sound processing unit 322 and a stimulator unit 324. Sound processing unit 322 receives an audio signals 323 from, for example, an upgrade module as described above. In the specific illustrated arrangement, audio signals 323 are delivered to a pre-processor 306 which filters the audio signals 323. Pre-processor 362 passes a signal component in a first frequency sub-band to an electrical stimulation signal processor 364, and passes a signal component in a second frequency sub-band to an acoustic stimulation signal processor 366. In certain embodiments, the first frequency sub-band comprises a high frequency portion of the audible frequency spectrum, while the second frequency sub-band comprises a low frequency portion of the audible frequency spectrum.

Electrical stimulation signal processor 364 and acoustic stimulation processor 366 each implement one or more sound encoding strategies to translate each portion of audio signals 323 provided thereto into electrical stimulation information, and acoustic stimulation information, respectively. Stimulator unit 324 comprises an electrical stimulation signal generator 372 to generate electrical stimulation signals based on the electrical stimulation information. Stimulator unit 324 also comprises an acoustic stimulation signal generator 374 to generate acoustic stimulation signals based on the acoustic stimulation information.

In the embodiments of FIG. 3, the cochlear implant further comprises one or more stimulation modules for delivering the electrical and acoustic stimulation signals to the recipient. In certain embodiments, the cochlear implant of comprise an electrode assembly implanted in the recipients cochlea for delivering the electrical stimulation signals, and a loudspeaker for delivering the acoustic stimulation signals. The loudspeaker may, for example, be any type of loudspeaker such as those commonly used with hearing aids.

In certain embodiments of FIG. 3, concurrent or substantially simultaneous acoustic and electrical stimulation of the cochlea is desirable so that the implant recipient does not perceive a delay between the two types of stimulations. Such a delay may bothersome to the implant recipient and interfere with the enjoyment and/or effectiveness of the recipient's hearing.

FIG. 3 illustrates specific embodiments of the present invention in which acoustic stimulation signals are used in conjunction with electrical stimulation signals to stimulate a recipient's cochlea. It would be appreciated that in alternative embodiments, mechanical stimulation signals may be used in place of the acoustic stimulation signals.

Figure 4:
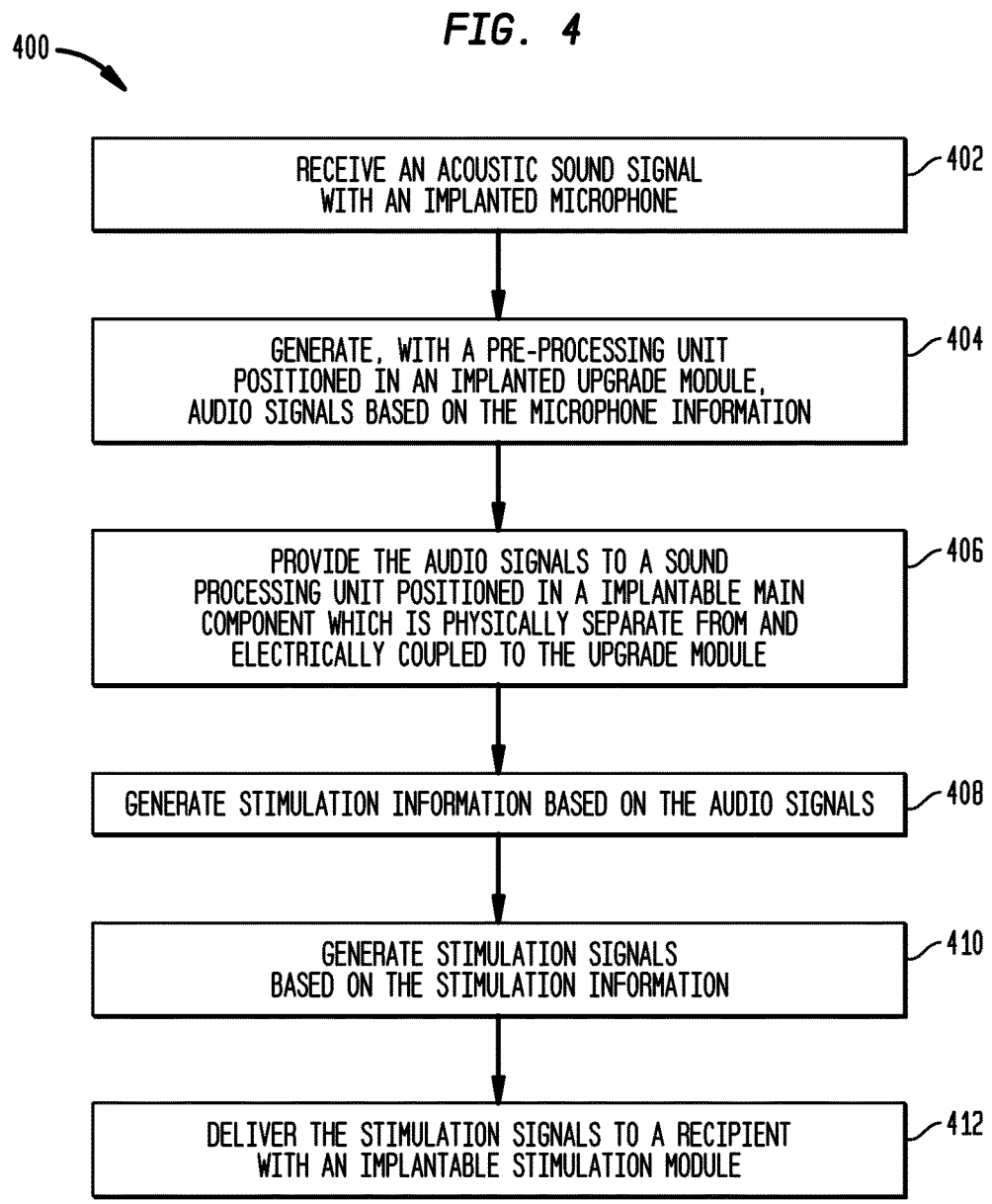
FIG. 4 is a flowchart illustrating a method of converting acoustic signals into a hearing percept, in accordance with embodiments of the present invention.

FIG. 4 is a flowchart illustrating a method 400 of converting acoustic signals into a hearing percept in accordance with embodiments of the present invention. Method 400 begins at block 402 where an acoustic sound signal is received by an implanted microphone. As discussed above, the microphone may be implanted in different locations within the recipient. In certain embodiments, the microphone is positioned in an implantable upgrade module.

At block 404, microphone information received from the implanted microphone is converted to audio signals. This conversion is performed by a pre-processing unit positioned in the upgrade module. As noted above, in certain embodiments, conversion of the microphone information into audio signals comprises suppressing body-noise detected by the microphone.

In certain embodiments, the implantable microphone comprises a first element configured to detect acoustic sound signals, and an accelerometer configured to detect movement of the recipient's skull. In these embodiments, converting the microphone information received from the implanted microphone into audio signals further comprises combining the detected acoustic sound signals and the output of the accelerometer to so as to suppress bone conducted sound detected by the first element of the microphone.

In still other embodiments, the hearing prosthesis comprises two or more microphones. In these embodiments, converting the microphone information received from the implanted microphone into audio signals further comprises combining the microphone information from the two or microphones in manner so as to substantially suppress bone conducted sound.

At block 406, the audio signals output by the pre-processing unit are provided to a sound processing unit positioned in a implantable main module which is physically separate from and electrically connected to the upgrade module. At block 408, the audio signals are converted by the sound processing unit into stimulation information. At block 410 a stimulator unit positioned in the implantable main module generates stimulation signals based on the stimulation information, and at block 412 the stimulation signals are delivered to the recipient with an implantable stimulation module.

As noted above, in certain embodiments of the present invention, the totally implantable hearing prosthesis comprises a cochlear implant configured to electrically stimulate the recipient's cochlea. In such embodiments, at block 408 the audio signals are converted into electrical stimulation information, and at block 410 the stimulator unit generates electrical stimulation signals. Furthermore, at block 412 the electrical stimulation signals are delivered to the recipient via a stimulation module in the form of an electrode assembly implanted in the recipient's cochlea.

Also as noted above, in other embodiments of the present invention, the hearing prosthesis is a bimodal cochlear implant. In such embodiments, at block 408 the audio signals are converted into electrical stimulation information and acoustic or mechanical stimulation information. At block 410 the stimulator unit generates electrical stimulation signals and acoustic or mechanical stimulation signals. Furthermore, at block 412 the electrical stimulation signals and acoustic or mechanical stimulation signals are delivered to the recipient via one or more stimulation modules. In such embodiments, bimodal cochlear implant comprises an electrode assembly implanted in the recipient's cochlea to deliver the electrical stimulation signals, and a loudspeaker or mechanical stimulator to deliver the acoustic or mechanical stimulation signals, respectively.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All patents and publications discussed herein are incorporated in their entirety by reference thereto.

What is claimed is:

1. A totally implantable hearing prosthesis comprising:
an implantable microphone configured to be implanted in a recipient and to detect sound signals that include body-borne noise;
an implantable upgrade module configured to be implanted in the recipient and to receive the sound signals from the implantable microphone, and comprising a preprocessing unit configured to convert the sound signals into noise-suppressed audio signals from which the body-borne noise has been substantially eliminated; and
an implantable main module, which is physically separate from and electrically connected to the upgrade module, configured to be implanted in the recipient and to receive the noise-suppressed audio signals from the upgrade module, and comprising:
a sound processing unit configured to generate stimulation information based on the noise-suppressed audio signals received from the preprocessing unit, and
a stimulator unit configured to generate stimulation signals based on the stimulation information; and
a stimulation module configured to be implanted in the recipient and to deliver the stimulation signals to the recipient.

2. The totally implantable hearing prosthesis of claim 1, wherein the stimulator unit is configured to generate electrical stimulation signals based on the stimulation information, and wherein the stimulation module comprises an electrode assembly implanted in a cochlea of the recipient to deliver the stimulation signals to the recipient.

3. The totally implantable hearing prosthesis of claim 2, wherein the stimulator unit is configured to generate electrical stimulation signals and acoustic stimulation signals based on the stimulation information, and wherein the hearing prosthesis further comprises:

a loudspeaker configured to deliver the acoustic stimulation signals to the recipient.

4. The totally implantable hearing prosthesis of claim 2, wherein the stimulator unit is configured to generate electrical stimulation signals and mechanical stimulation signals based on the stimulation information, and wherein the hearing prosthesis further comprises:
an implanted mechanical stimulator configured to deliver the mechanical stimulation signals to the recipient.

5. The hearing prosthesis of claim 1, wherein the upgrade module further comprises:
a rechargeable battery.

6. The totally implantable hearing prosthesis of claim 1, wherein the implantable microphone is positioned in the upgrade module.

7. The totally implantable hearing prosthesis of claim 1, wherein the implantable microphone comprises:
a first element configured to detect the sound signals, wherein the sound signals include air-conducted sounds and bone-conducted sounds; and
an accelerometer configured to detect movement of a skull of the recipient,
wherein the preprocessing unit is configured to utilize the movement of the skull of the recipient detected by the accelerometer to suppress the bone-conducted sounds detected by the first element of the microphone.

8. The totally implantable hearing prosthesis of claim 1, wherein the implantable microphone comprises a first implantable microphone, and wherein the totally implantable hearing prosthesis comprises a second implantable microphone, and wherein the first and second implantable microphones are configured to detect first and second sets of sound signals, respectively, that each include air-conducted sounds and bone-conducted sounds, and wherein the preprocessing unit is configured to combine the first and second sets of sound signals to substantially suppress the bone-conducted sounds.

9. The totally implantable hearing prosthesis of claim 1, further comprising:
a transceiver positioned in the upgrade module, wherein the transceiver is configured to provide a bi-directional energy transfer link with an external device.

10. An implantable hearing prosthesis method, comprising:
detecting, at an implantable microphone configured to be implanted in a recipient, sound signals comprising air-conducted sounds and bone-conducted sounds;
receiving, at a pre-processing unit positioned in an implantable upgrade module, the sound signals from the implantable microphone;
converting, with the pre-processing unit, the sound signals into noise-suppressed audio signals from which the bone-conducted sounds have been substantially reduced;
providing the noise-suppressed audio signals to a sound processing unit positioned in an implantable main module that is physically separate from, and electrically connected to, the upgrade module;
generating, with the sound processing unit, stimulation information based on the noise-suppressed audio signals;
generating, with a stimulator unit positioned in the implantable main module, stimulation signals based on the stimulation information; and
delivering the stimulation signals to the recipient.

11. The method of claim 10, further comprising:
generating, with the stimulator unit positioned in the implantable main module, electrical stimulation signals and acoustic stimulation signals based on the stimulation information;
delivering the electrical stimulation signals to a recipient with an electrode assembly implanted in a cochlea of the recipient; and
delivering the acoustic stimulation signals to a recipient with an implanted loudspeaker.

12. The method of claim 11, further comprising:
concurrently delivering the electrical stimulation signals and the acoustic stimulation signals to the recipient.

13. The method of claim 10, wherein the implantable microphone is positioned in the upgrade module.

14. The method of claim 10, wherein the implantable microphone comprises a first element configured to detect the sound signals, and an accelerometer configured to detect movement of a skull of the recipient, and wherein converting the sound signals into noise-suppressed audio signals from which the bone-conducted sounds have been substantially reduced comprises:
combining the detected sound signals and an output of the accelerometer to so as to suppress bone-conducted sounds detected by the first element of the microphone.

15. The method of claim 10, wherein the implantable microphone comprises a first implantable microphone, and wherein the hearing prosthesis comprises a second implantable microphone, and wherein the first and second implantable microphones are configured to detect first and second sets of sound signals, respectively, and wherein converting the sound signals into noise-suppressed audio signals from which the bone-conducted sounds have been substantially reduced comprises:
combining the first and second sets of sound signals to substantially suppress bone-conducted sound.

16. The method of claim 10, further comprising:
generating, with the stimulator unit positioned in the implantable main module, electrical stimulation signals based on the stimulation information; and
delivering the electrical stimulation signals to a recipient with an electrode assembly implanted in a cochlea of the recipient.

17. The method of claim 10, further comprising:
generating, with the stimulator unit positioned in the implantable main module, electrical stimulation signals and mechanical stimulation signals based on the stimulation information;
delivering the electrical stimulation signals to a recipient with an electrode assembly implanted in a cochlea of the recipient; and
delivering the mechanical stimulation signals to a recipient with an implanted mechanical stimulator.

* * * * *